US011871910B2

(12) United States Patent
Kort

(10) Patent No.: US 11,871,910 B2
(45) Date of Patent: Jan. 16, 2024

(54) VAGINAL SPECULUM AND SYSTEM

(71) Applicant: Dan Kort, El Centro, CA (US)

(72) Inventor: Dan Kort, El Centro, CA (US)

( * ) Notice: Subject to any disclaimer, the term of this patent is extended or adjusted under 35 U.S.C. 154(b) by 311 days.

(21) Appl. No.: 17/223,951

(22) Filed: Apr. 6, 2021

(65) Prior Publication Data

US 2021/0315450 A1 Oct. 14, 2021

Related U.S. Application Data

(60) Provisional application No. 63/008,728, filed on Apr. 11, 2020, provisional application No. 63/053,399, filed on Jul. 17, 2020.

(51) Int. Cl.
*A61B 1/303* (2006.01)
*A61B 1/32* (2006.01)
*A61B 1/06* (2006.01)

(52) U.S. Cl.
CPC ............... *A61B 1/303* (2013.01); *A61B 1/06* (2013.01); *A61B 2217/005* (2013.01)

(58) Field of Classification Search
CPC .. A61B 1/303; A61B 1/32; A61B 1/31; A61B 1/06; A61B 2217/005; A61B 17/42; A61B 17/4208; A61B 17/4241; A61B 17/425
See application file for complete search history.

(56) References Cited

U.S. PATENT DOCUMENTS

| | | | | |
|---|---|---|---|---|
| 3,789,829 | A * | 2/1974 | Hasson | A61N 5/1016 600/221 |
| 4,130,113 | A * | 12/1978 | Graham | A61B 17/0293 600/224 |
| 5,209,754 | A * | 5/1993 | Ahluwalia | A61B 17/4241 606/1 |
| 5,509,893 | A * | 4/1996 | Pracas | A61B 1/32 600/184 |
| 8,608,652 | B2 * | 12/2013 | Voegele | A61B 1/303 600/210 |
| 8,690,767 | B2 * | 4/2014 | Kecman | A61B 1/32 600/222 |
| 9,861,349 | B2 * | 1/2018 | Nadershahi | A61B 17/0218 |
| 10,174,933 | B2 * | 1/2019 | Phillips, Jr. | A61B 1/32 |
| 2019/0254651 | A1 * | 8/2019 | Coale | A61M 29/00 |

* cited by examiner

*Primary Examiner* — Kevin T Truong
*Assistant Examiner* — Tracy L Kamikawa
(74) *Attorney, Agent, or Firm* — CP LAW GROUP PC; Cy Bates

(57) ABSTRACT

A vaginal speculum and system include a plurality of pivoting blades coupled to a housing having an aperture. The plurality of pivoting blades is coupled to a cam plate, and upon rotation of the cam plate, the plurality of pivoting blades are configured to go from a collapsed state to an expanded state. The system further includes an insert having a vaginal seal at a distal end and a plurality of ports at a proximal end. The vaginal speculum and system are configured for use in medical diagnostic and treatment procedures by opening the vagina of a patient in multiple directions for mitigating potential obstruction of view such that a practitioner may fully visualize the cervix and properly inspect and diagnose cervical conditions or the absence thereof.

7 Claims, 13 Drawing Sheets

VAGINAL SPECULUM AND SYSTEM

CROSS-REFERENCE TO RELATED APPLICATIONS

This application claims benefit of priority with U.S. Provisional Application Ser. No. 63/008,728, filed Apr. 11, 2020, and additionally claims benefit of priority with U.S. Provisional Application Ser. No. 63/053,399, filed Jul. 17, 2020; the entire contents of which are hereby incorporated by reference.

BACKGROUND

Field of the Invention

This invention relates to medical devices; and more particularly, to a system including a speculum for use in medical diagnostic and treatment procedures.

Description of the Related Art

Vaginal specula are generally used to dilate the vagina and visualize the uterine cervix to screen and treat for benign and cancerous lesions of the cervix. Generally, existing vaginal specula are two-bladed, and often include a stationary blade that remains fixed relative to the speculum handle, and a pivoting blade. The stationary and pivoting blades are generally substantially limited to moving apart and back together in relation to one axis.

There are several drawbacks to existing speculum designs. The most important of these is the potential failure to fully visualize the cervix which could lead to failure to diagnose cervical cancer-a life-threatening condition. In some women, with the two-bladed speculum, the vaginal walls collapse between the two-blades and obscure the view of the cervix. Additionally, the current two-blade design has relatively large blades that are difficult to introduce into the vagina of an apprehensive patient.

Finally, typical speculums are not designed to provide a seal between the device and the patient's vagina for enabling certain procedures, such as, without limitation, maintaining a seal when used in conjunction with a laparoscopic procedure and allowing a complete vaginal hysterectomy wherein the cervix can be removed.

SUMMARY

The invention is directed to a system including: a novel vaginal speculum and an insert configured to engage the speculum, the insert further providing a vaginal seal and a plurality of ports for enabling a medical procedure.

In various embodiments, the vaginal speculum system provides a seal between the device and the patient's vagina for enabling certain procedures, such as, without limitation, maintaining a seal when used in conjunction with a laparoscopic procedure and allowing a complete vaginal hysterectomy wherein the cervix can be removed. If additional visualization is required, the CO2 distention will allow more room distally and a better view.

The speculum generally includes: a fixed blade, and a plurality of pivoting blades each being hingedly coupled to a housing of the speculum, wherein each of the plurality of pivoting blades is characterized as including a follower element disposed at a proximal end and a spoon element disposed at a distal end thereof; and the vaginal speculum further including a cam plate comprising a number of corresponding grooves, each groove being configured to engage the follower element of one of the plurality of pivoting blades, wherein rotation of the cam plate achieves, depending on direction of rotation and orientation of the grooves, radial expansion or collapse of the plurality of pivoting blades relative to the fixed blade, thereby configuring the vaginal speculum between a collapsed state and an expanded state.

The hinged portions formed at the mating of the housing and pivoting blades are maintained outside of and away from vaginal tissue to mitigate potential for injury or discomfort to a patient.

The plurality of pivoting blades opens the vagina of a patient in multiple directions for mitigating potential for obstruction of view such that a practitioner may fully visualize the cervix and properly inspect and diagnose cervical conditions or the absence thereof.

Additionally, the plurality of blades allows for a smaller blade-size and a minimally invasive insertion profile.

The speculum described herein allows access into the uterine cavity for placing intrauterine devices (IUDs), and performing endometrial biopsies, hysteroscopy, and the like.

The insert accessory ("insert") provides a plurality of ports at a proximal end of the insert, and a vaginal seal at a distal end thereof, wherein the vaginal seal is configured to provide a hermetic seal of the device at the vaginal opening.

These and other features and advantages are further detailed in the appended detailed description of embodiments.

BRIEF DESCRIPTION OF THE DRAWINGS

These, and other features and embodiments, will be further appreciated in the appended detailed descriptions, in particular, when reviewed in conjunction with the drawings, wherein.

DETAILED DESCRIPTION

Figure 1:
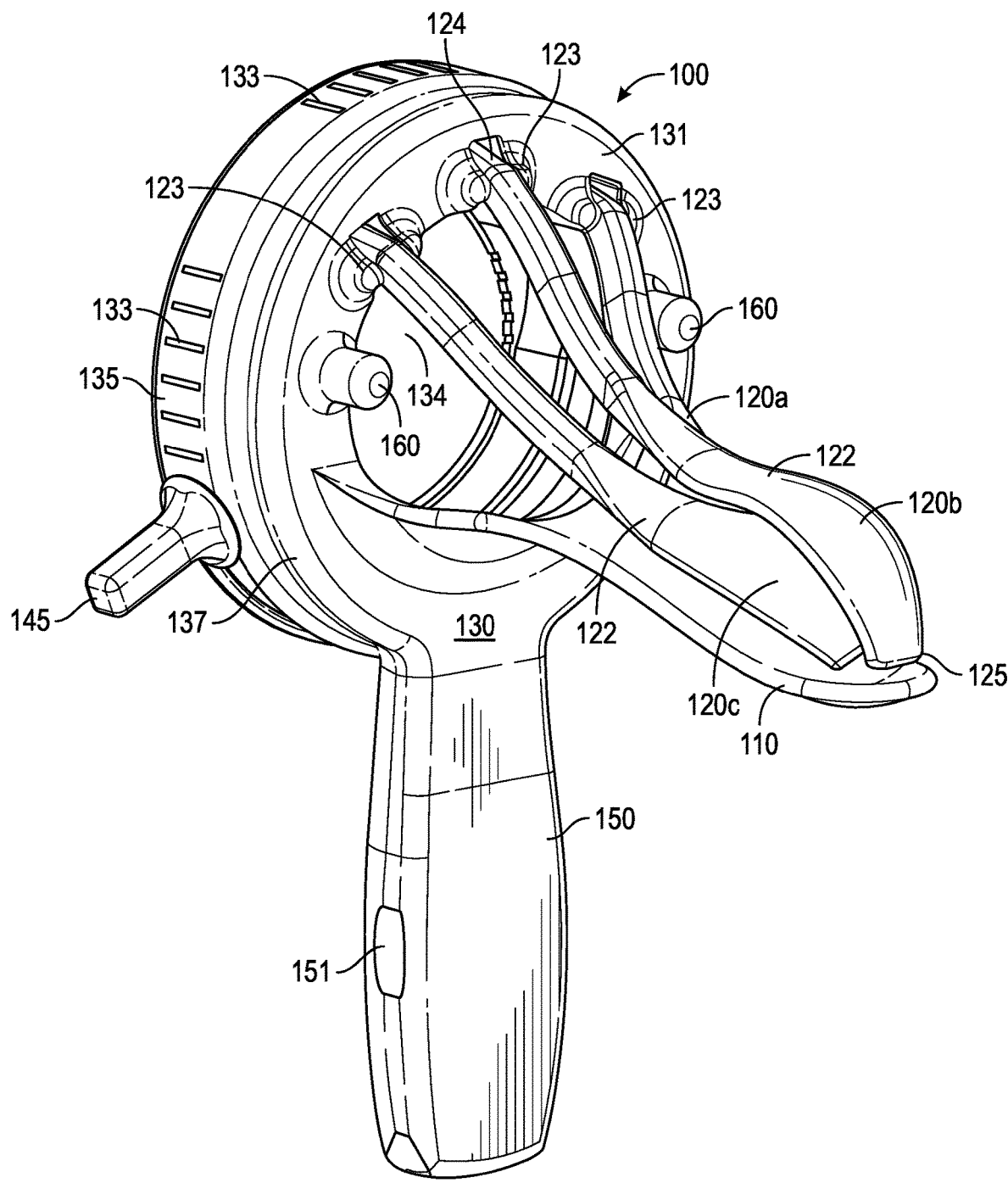
FIG. 1 shows a perspective view of a vaginal speculum, including a front, top, and left-side of the vaginal speculum in accordance with a first illustrated embodiment.

In the following description, for purposes of explanation and not limitation, details and descriptions are set forth in order to provide a thorough understanding of the embodiments of the invention. However, it will be apparent to those skilled in the art that the present invention may be practiced in other embodiments, including certain variations or alternative combinations that depart from these details and descriptions. The illustrated examples are intended to enable those with skill in the art to practice the invention, but such examples shall not reasonably be construed as limiting the spirit and scope of the invention as-claimed.

For purposes herein, the term "lever" means an element configured to receive an input force on one end apply a subsequent force to the other.

The term "speculum" means an instrument that is used to dilate an orifice or canal in the body to allow for inspection.

The term "right-hand operation" means a lever located on the right side of the housing relative to a practitioner's perspective, whereby the practitioner holds the vaginal speculum with their left hand at an elongated handle and adjusts and tightens the lever with their right hand.

The term "left-hand operation" means a lever located on the left side of the housing relative to a practitioner's perspective, whereby the practitioner holds the vaginal speculum with their right hand at an elongated handle and adjusts and tightens the lever with their left hand.

Unless explicitly defined herein, terms are to be construed in accordance with the plain and ordinary meaning as would be appreciated by one having skill in the art.

General Embodiments

In a first embodiment, a vaginal speculum for use with a medical system is disclosed, the vaginal speculum comprises a housing having a distal surface and a proximal surface, an aperture extending through the housing from the distal surface to the proximal surface, a fixed blade coupled to the distal surface, and a plurality of pivoting blades each hingedly coupled to the distal surface. Each of the plurality of pivoting blades comprises a follower element at a first end and a spoon element at a second end; and a cam plate disposed within the housing. The cam plate comprises a plurality of grooves, wherein each follower element is configured to engage with one of the plurality of grooves. The plurality of pivoting blades is configured to expand or collapse relative to the fixed blade upon rotation of the cam plate.

In some embodiments, the vaginal speculum may further comprise an elongated handle coupled to the housing.

Generally, the vaginal speculum may further comprise a lever coupled to the cam plate, wherein the cam plate is configured to rotate upon movement of said lever.

In some embodiments, the vaginal speculum may further comprise one or more light-guiding elements disposed on the distal surface. The vaginal speculum may include an actuator electrically coupled to the one or more light-guiding elements.

In some embodiments, the house may further comprise a plurality of notches disposed on the housing.

In some embodiments, the vaginal speculum may further comprise a port attachment configured to couple to the housing and extend through the aperture, the port attachment being configured to receive and guide a surgical instrument therethrough.

In a second embodiment, a vaginal speculum is disclosed. The vaginal speculum comprises a housing having a distal surface and a proximal surface and an aperture extending through the housing from the distal surface to the proximal surface. The vaginal speculum further comprises a plurality of pivoting blades each having a first end and a second end, the plurality of pivoting blades is hingedly coupled to the distal surface at the first end, and wherein the plurality of pivoting blades is configured to expand and collapse relative to the second end.

In some embodiments, the vaginal speculum may further comprise a fixed blade coupled to the distal surface.

Generally, the vaginal speculum may further comprise a follower element disposed at the first end of each of the plurality of pivoting blades, and a cam plate disposed within the housing. The cam plate comprises a plurality of grooves wherein each follower element is configured to engage with one of the plurality of grooves.

In some embodiments, the vaginal speculum may further comprise a lever coupled to the cam plate, wherein the cam plate is configured to rotate upon movement of said lever.

In some embodiments the vaginal speculum may further comprise one or more light-guiding elements disposed on the distal surface.

In some embodiments the vaginal speculum may further comprise an actuator electrically coupled to the one or more light-guiding elements.

In some embodiments the vaginal speculum may further comprise a plurality of notches disposed on the housing.

In some embodiments the vaginal speculum may further comprise a port attachment configured to couple to the housing and extend through the aperture, the port attachment being configured to receive and guide a surgical instrument therethrough.

In a third embodiment, a system for performing a medical procedure is disclosed. The system comprises a vaginal speculum and an insert. The vaginal speculum comprises a housing having a distal surface and a proximal surface, an aperture extending through the housing from the distal surface to the proximal surface, a fixed blade coupled to the distal surface, and a plurality of pivoting blades each hingedly coupled to the distal surface. The plurality of pivoting blades each comprises a follower element at a first end and a spoon element at a second end. A cam plate is disposed within the housing and comprises a plurality of grooves, wherein each follower element is configured to engage with one of the plurality of grooves. The plurality of pivoting blades is configured to expand or collapse relative to the fixed blade upon rotation of the cam plate. The insert comprises a proximal end and a distal end and further comprises a plurality of ports at the proximal end, and a vaginal seal at the distal end disposed between the housing and spoon elements.

In some embodiments the vaginal seal may comprise an annular shape.

In some embodiments the insert may further comprise a gas deployment-element disposed at the proximal end, wherein the gas deployment-element is configured to deploy gas from an external source into a vaginal cavity during a procedure.

In some embodiments the insert may further comprise a vacuum deployment-element disposed at the proximal end, wherein the vacuum deployment-element is configured to remove gaseous matter from a vaginal cavity.

In an alternative embodiment, the vaginal speculum may comprise no fixed blade, this configuration would allow access to the posterior vaginal wall, the sacrospinous ligament and the perineum for repairs as needed. For example, the speculum may comprise only a plurality of pivoting blades each being hingedly coupled to a housing of the vaginal speculum, wherein each of the plurality of pivoting blades is characterized as including a follower element disposed at a proximal end and a spoon element disposed at a distal end thereof. In this regard, two or more pivoting blades are actuated by the cam plate to open and close access to the vagina.

In another embodiment, the vaginal speculum may comprise two or more fixed blades.

The vaginal speculum may comprise one or more light projecting elements. The light projecting elements may comprise light emitting diodes, filaments configured to communicate light from a light source, or any other conventional lighting component as may be appreciated by one having skill in the art.

The vaginal speculum is preferably manufactured using a conventional injection molding technique and therefore can comprise a thermoplastic material, such as acrylonitrile butadiene styrene (ABS), polycarbonate, or other thermoplastic material. Other manufacturing techniques and material compositions will be apparent to one having skill in the art and may be alternatively practiced. For example, other plastic molding techniques may be similarly employed, or alternatively, the vaginal speculum may be cast or otherwise manufactured from metal materials, including stainless steel, aluminum and the like. In some embodiments, the vaginal speculum can embody an assembly including a plurality of individual components or sub-assemblies each comprising the same or different material compositions.

The vaginal speculum is generally used by inserting a second end of the blades (spoon elements) into the vaginal cavity of a patient with the speculum in the collapsed state, and rotating the cam plate, generally using a knob or lever coupled to the cam plate, such that a turn of the cam plate corresponds to translation of the corresponding follower elements of the plurality of pivoting blades within their respective grooves of the cam plate, thereby effectuating a hinged expansion of the pivoting blades relative to the fixed blade from the collapsed state to an expanded state and opening the vaginal cavity for viewing vaginal and cervical tissue.

First Illustrated Embodiment—Vaginal Speculum

Turning now to the drawings, FIG. 1 shows a perspective view of a vaginal speculum (100), including a front, top, and left-side of the vaginal speculum in accordance with a first illustrated embodiment. The vaginal speculum comprises a fixed blade (110), and a plurality of pivoting blades (120a; 120b; and 120c) each being hingedly coupled to a housing (130) of the vaginal speculum at a distal surface (131), via a hinge element (123), wherein each of the plurality of pivoting blades is characterized as including a follower element (121) disposed at a first end (124) and a spoon element (122) disposed at a second end (125) thereof. The housing includes a body (137), a cam housing (135) and an aperture (134) extending through the housing.

The cam plate (FIG. 5, 140) is operatively coupled to a lever (145), such that a user may rotate the lever to effectuate rotation of the cam plate for purposes of configuring the vaginal speculum (100) between the collapsed and expanded states.

Figure 13:
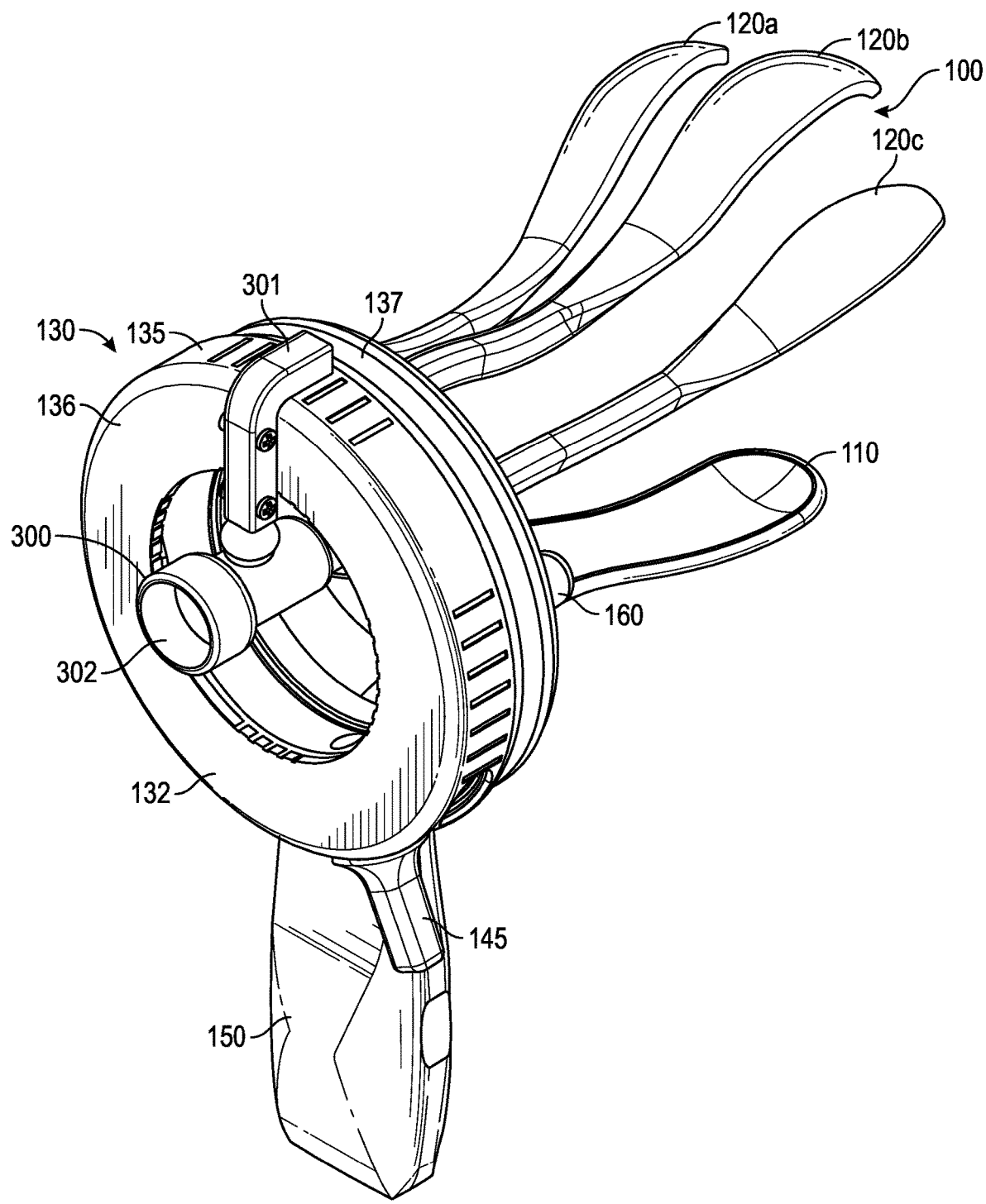
FIG. 13 shows an alternative system, wherein a vaginal speculum is combined with a single-port attachment in accordance with a third illustrated embodiment.

In some embodiments, the housing may comprise a plurality of notches (133) disposed around a periphery thereof. The notches can be used to locate an accessory, for example, as shown in FIG. 13.

In some embodiments, the blades may be held in the open position by tightening the lever (145) and engaging the threaded member (146) about the device. Other clamping, pinning, and ratcheting-type mechanisms can be similarly deployed by one having skill in the art for the purpose of locking and unlocking the blades between the expanded and collapsed states.

The vaginal speculum (100) may also comprise an elongated handle (150) extending from the housing (130). The handle preferably includes an ergonomic design for providing comfort and stabilization over an extended operating duration.

In certain embodiments, the vaginal speculum may comprise one, two, three, or more light-guiding elements (160). The light guiding elements may comprise a light source, such as a light emitting diode, or may be otherwise configured to communicate light from a light source, such as, for example and without limitation, a fiber optic or plastic filament configured to communicate light emitted from a light source in a direction into the vagina with the vaginal speculum (100) configured in the expanded state. In this regard, the light source may be housed within the elongated handle (150) of the vaginal speculum, or another part of the housing (130). The light from the light source may comprise white light, ultraviolet light, or other light as may be desired, and may be switched there between, depending on the procedure and practitioner's needs. An actuator (151) can be provided which is electrically coupled to light source and/or light-guiding element for turning the light-guiding element from an on state to an off state, and vice versa.

Figure 2:
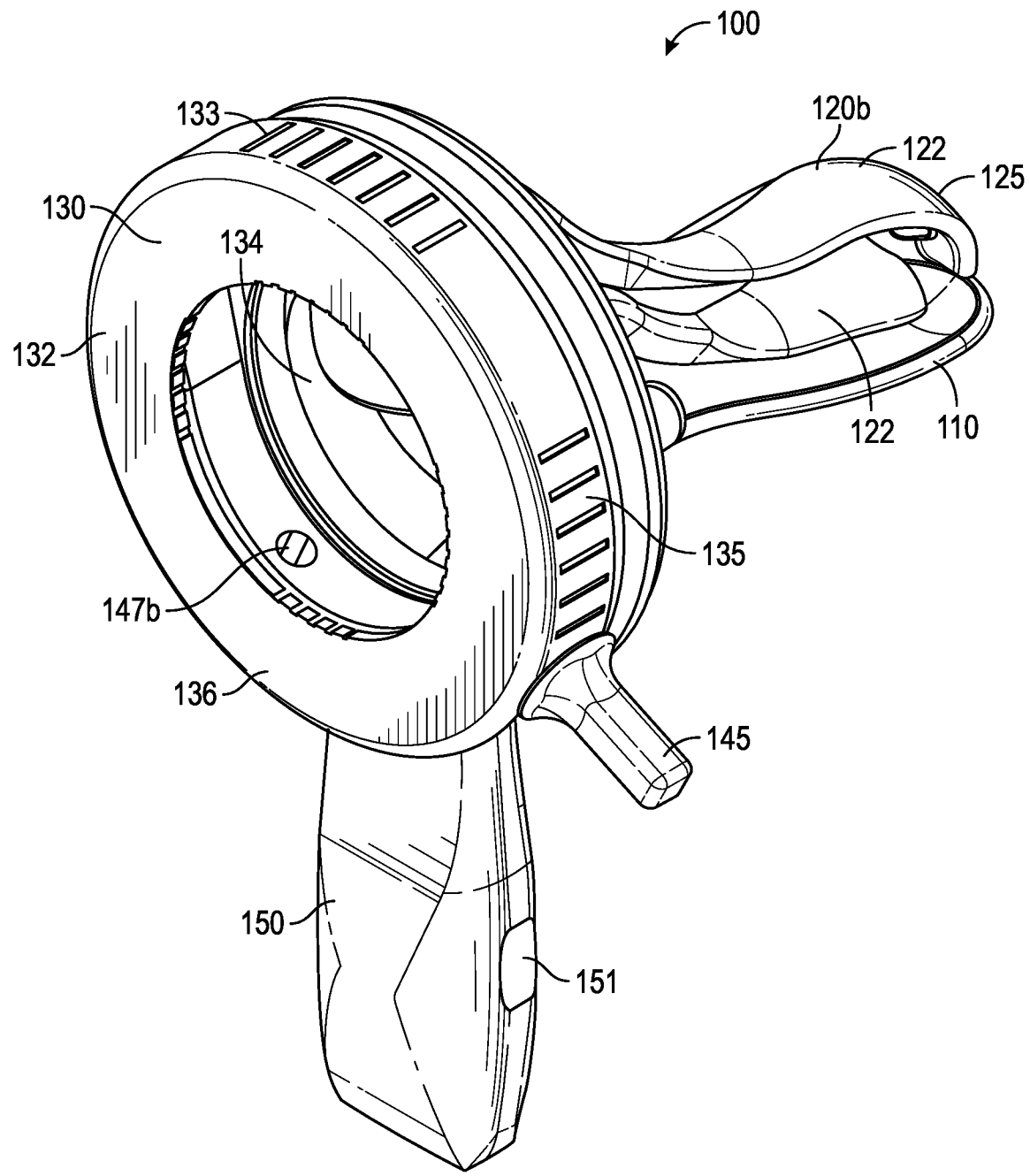
FIG. 2 shows another perspective view, including a rear, top, and right-side of the vaginal speculum in accordance with the first illustrated embodiment.

FIG. 2 shows another perspective view, including a rear, top, and right-side of the vaginal speculum (100) in accordance with the first illustrated embodiment. The vaginal speculum includes a plurality of pivoting blades (120b; 120c) and a fixed blade (110) coupled to a housing (130) at a distal surface (FIG. 1, 131). A proximal surface (132), opposite the distal surface, is shown having an aperture (134) extending therethrough, which allows a practitioner access to a vaginal cavity for inspection and possible medical procedure. The housing includes a cam housing (135) wherein a cam plate (FIG. 5, 140) is contained within, and a cover (136) to protect said cam plate. A lever (145) is shown coupled to the cam housing and is operatively coupled to the cam plate wherein upon movement of the lever, the cam plate rotates, causing the plurality of pivoting blades to change from a collapsed state to an expanded state, or alternatively, from an expended state to a collapsed state.

The housing (130) additionally includes other optional features such as an elongated handle (150) and an actuator (151). The actuator is disposed on the elongated handle and is electrically coupled to a light source for actuation of the light-guiding element (160). In other embodiments, the button may be disposed on alternative parts of the housing while remaining electrically coupled to the light source, thereby allowing a light-guiding element to be turned on or off. As shown, a plurality of notches (133) is disposed on the housing which are used in conjunction with attachments or accessories coupled to the vaginal speculum (100). Additionally, a threaded receiver (147b) is shown disposed on the housing which allows the vaginal speculum to be converted from a right-handed operation to a left-handed operation by relocating the lever (145) to an opposite side. Typically, one hand will hold the vaginal speculum at the elongated handle and an alternative hand will move the lever to a desired position and subsequently tightened to maintain the vaginal speculum in the desired position. Other means of expanding and collapsing the vaginal speculum will be appreciated by one having skill in the art, including means such as holding the elongated handle and applying force to the lever with a single hand. In other embodiments, a motor is utilized to mechanically provide an input force which causes the vaginal speculum to expand and/or collapse.

Figure 3:
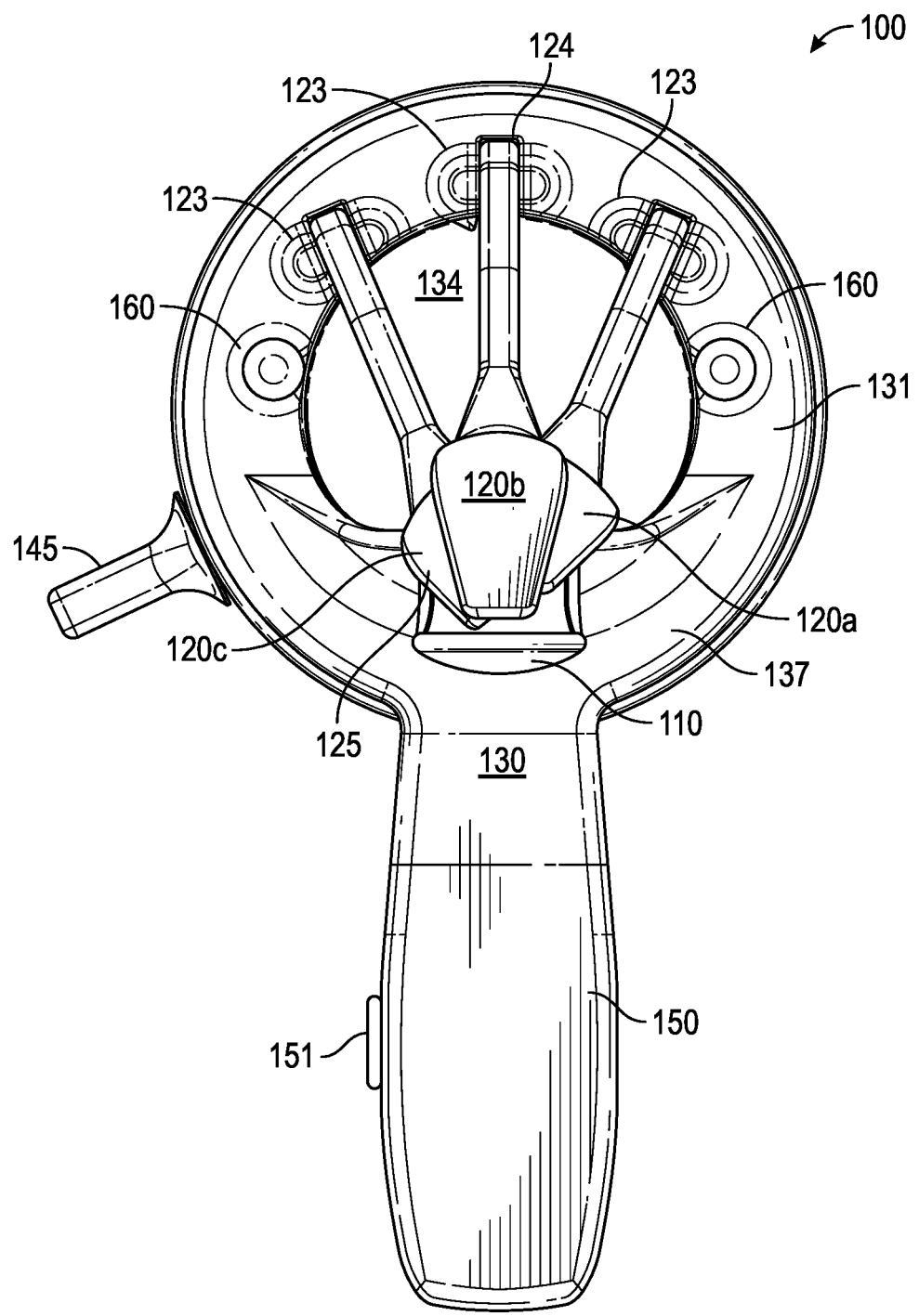
FIG. 3 shows a front plan view of the vaginal speculum in accordance with the first illustrated embodiment.

FIG. 3 shows a front plan view of the vaginal speculum (100) in accordance with the first illustrated embodiment. The vaginal speculum comprises housing (130) having a distal surface (131) wherein an aperture (134) extends therethrough. Coupled to the distal surface is a plurality of pivoting blades (120a; 120b; 120c) via a hinge element (123) at a first end (124) for each of the plurality of pivoting blades. As shown, the plurality of pivoting blades is coupled to an upper portion of the aperture. At a bottom portion of the aperture, a fixed blade (110) is coupled therewith. In a collapsed state, the plurality of pivoting blades and the fixed blade converge near a second end (125), thereby allowing for ease of insertion into a patient. Once the vaginal speculum is inserted, the plurality of pivoting blades can then be expanded to a desired position. As illustrated, a lever (145) is shown to control movement of the plurality of pivoting blades. In other embodiments, alternative means are used. An example may include the housing (130) further comprising a rotatable portion surrounding the distal surface configured to rotate like a dial, wherein in one direction the rotatable portion causes the plurality of pivoting blades to expand, and in an opposite direction the rotatable portion causes the plurality of pivoting blades to collapse. Another example may include use of a motor which causes the plurality of pivoting blades to expand and collapse.

Figure 4:
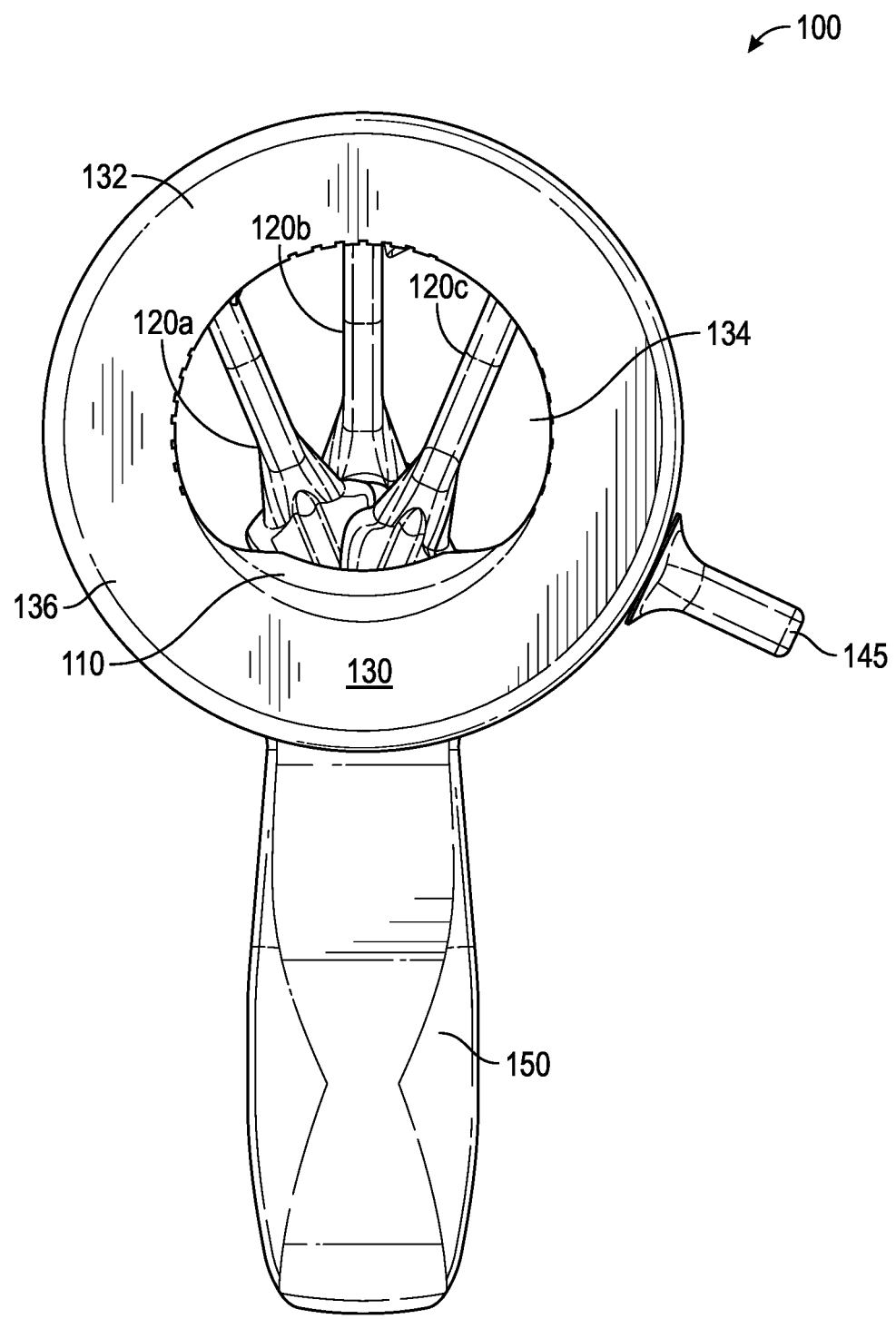
FIG. 4 shows a rear plan view of the vaginal speculum in accordance with the first illustrated embodiment.

FIG. 4 shows a rear plan view of the vaginal speculum (100) in accordance with the first illustrated embodiment. The vaginal speculum includes a housing (130) having a proximal surface (132) and an aperture (134) extending though the proximal surface, which allows for proper view and access by a practitioner. The vaginal speculum as shown is in a collapsed state wherein a plurality of pivoting blades (120a; 120b; 120c) are obstructing view through the aperture. Upon turning a lever (145) or other means of actuation, the plurality of pivoting blades will expand relative to a fixed blade (110) to allow view and access through said aperture. An optional elongated handle (150) is coupled to the housing for ease of holding the vaginal speculum. The proximal surface and aperture are each illustrated as having an annular periphery, however, other shapes can be utilized as can be appreciated by one having skill in the art.

In an exemplary embodiment, the aperture (134) comprises an area larger than current instruments known in the prior art. Typical instruments comprise apertures having an area up to 16.5 cm$^2$, in comparison to the exemplary embodiment comprising an area of 28 cm$^2$. Increasing the aperture area allows more instruments to be used in conjunction with the vaginal speculum (100). This ability to use more instruments in a procedure allows the vaginal speculum to be used in more experimental surgical techniques known as natural orifice transluminal endoscopic surgery (NOTES) due to an increase of access to the abdominal cavity.

Figure 5:
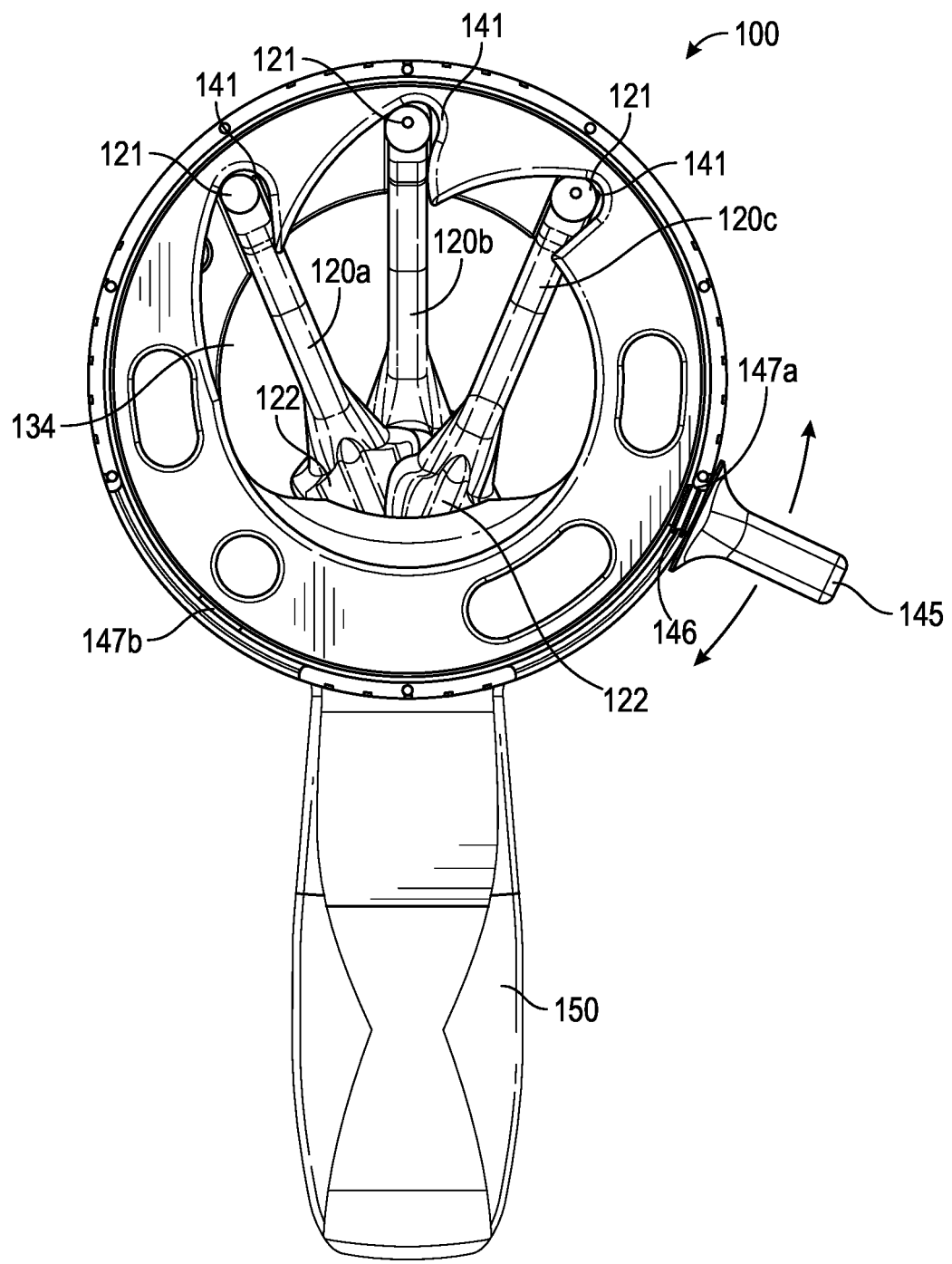
FIG. 5 shows a rear plan view of the vaginal speculum with inner componentry exposed in accordance with the first illustrated embodiment.

FIG. 5 shows a rear plan view of the vaginal speculum (100) with inner componentry exposed in accordance with the first illustrated embodiment. The vaginal speculum includes a plurality of pivoting blades (120a; 120b; 120c) hingedly coupled to a housing (130), wherein each of the plurality of pivoting blades comprises a spoon element (122) and a follower element (121). The vaginal speculum further includes a cam plate (140) comprising a number of corresponding grooves (141), each groove being configured to engage the follower element of one of the plurality of pivoting blades, wherein rotation of the cam plate achieves, depending on direction of rotation and orientation of the grooves, radial expansion or collapse of the plurality of pivoting blades relative to a fixed blade (110), thereby configuring the vaginal speculum between a collapsed state and an expanded state.

Rotation of the cam plate (140) is achieved by a lever (145) operatively coupled to the cam plate via a threaded member (146) coupled to a threaded receiver (147a). The lever is configured to decouple from the threaded receiver (147a) and move to another threaded receiver (147b) depending on desired position of the lever by a practitioner. Factors such as which hand will hold an elongated handle (150), which hand will apply force to the lever, and which direction of the lever will cause the plurality of pivoting blades to expand will all be factors when determining desired position of the lever. As shown, pressing the lever downwards (clockwise) will cause the grooves (141) to apply a downward force on each follower element (121), which therefore causes the spoon elements (122) of the plurality of pivoting blades to expand. It will be appreciated by one having skill in the art that if the lever were coupled to the threaded receiver (147b) on an opposite side of the elongated handle, then the lever would need to be pushed upward (clockwise) to expand the plurality of pivoting blades. In alternative embodiments, an opposite configuration is achieved wherein a counter-clockwise movement of the lever causes the plurality of pivoting blades to expand.

Figure 6:
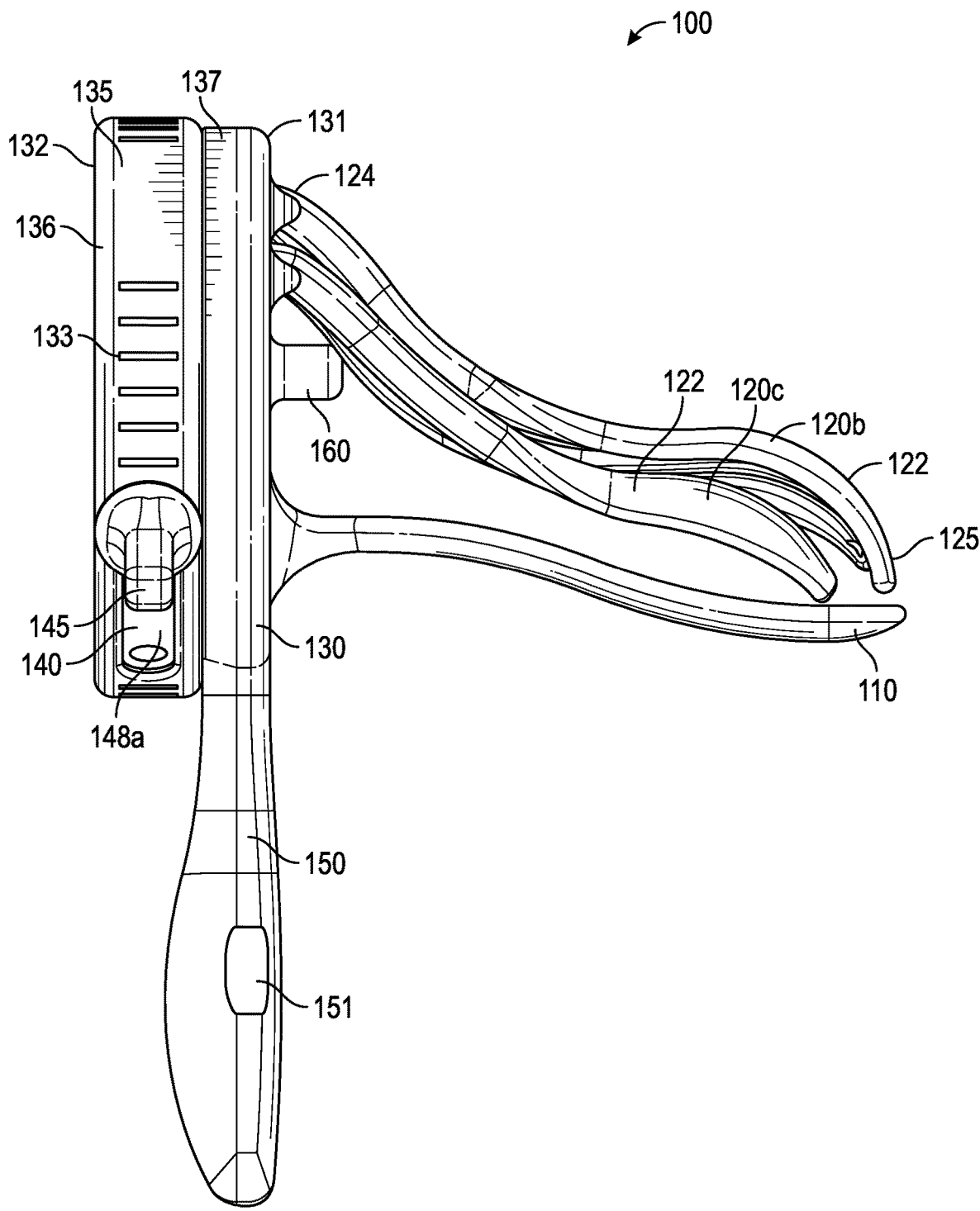
FIG. 6 shows a left plan view of the vaginal speculum in accordance with the first illustrated embodiment.

FIG. 6 shows a left plan view of the vaginal speculum (100) in accordance with the first illustrated embodiment. The vaginal speculum includes a housing (130) having a body (137), a cam housing (135), and a cover (136). Disposed within the cam housing and between the cover and body is a cam plate (140). A plurality of pivoting blades (120b; 120c) are hingedly coupled to the body at a first end (124). Spoon elements (122) are disposed on the plurality of pivoting blades at a second end (125), and while in a collapsed state (as shown), the spoon elements converge with a fixed blade (110). A number of light-guiding elements (160) are used to improve a practitioner's ability to see. An actuator (151) is disposed on an elongated handle (150), the elongated handle being coupled to the housing. Upon engagement of the actuator, light will emit from the light-guiding elements. Expansion of the plurality of pivoting blades is caused by a force being applied to a lever (145) which causes the cam plate to rotate. Once a desired expansion of the plurality of pivoting blades has been achieved, a locking mechanism can be used to maintain the plurality of pivoting blades in a fixed state. Means of locking may include coupling a threaded member into a threaded slot or a press button wherein upon pressing inwards the press button creates a friction fit.

As shown, the spoon elements (122) located at the second end (125) each comprise a curvature. The curvature allows for each second end of the plurality of pivoting blades (120a; 120b; 120c) to conform closer to one another while in a collapsed state. This allows for a reduced insertion surface area which will in turn decrease discomfort to a patient during beginning stages of a procedure. The curvature also increases surface area of each of the plurality of pivoting blades which contacts the patient. The increased surface area in addition to use of the plurality of pivoting blades increases overall area of contact compared to a single-blade speculum, and therefore reduces pressure to the patient. Additionally, the fixed blade (110) comprises a bend between the housing (130) and the second end. The bend of the fixed blade allows for the vaginal speculum to resist horizontal forces which may push the vaginal speculum out during the procedure.

Figure 7:
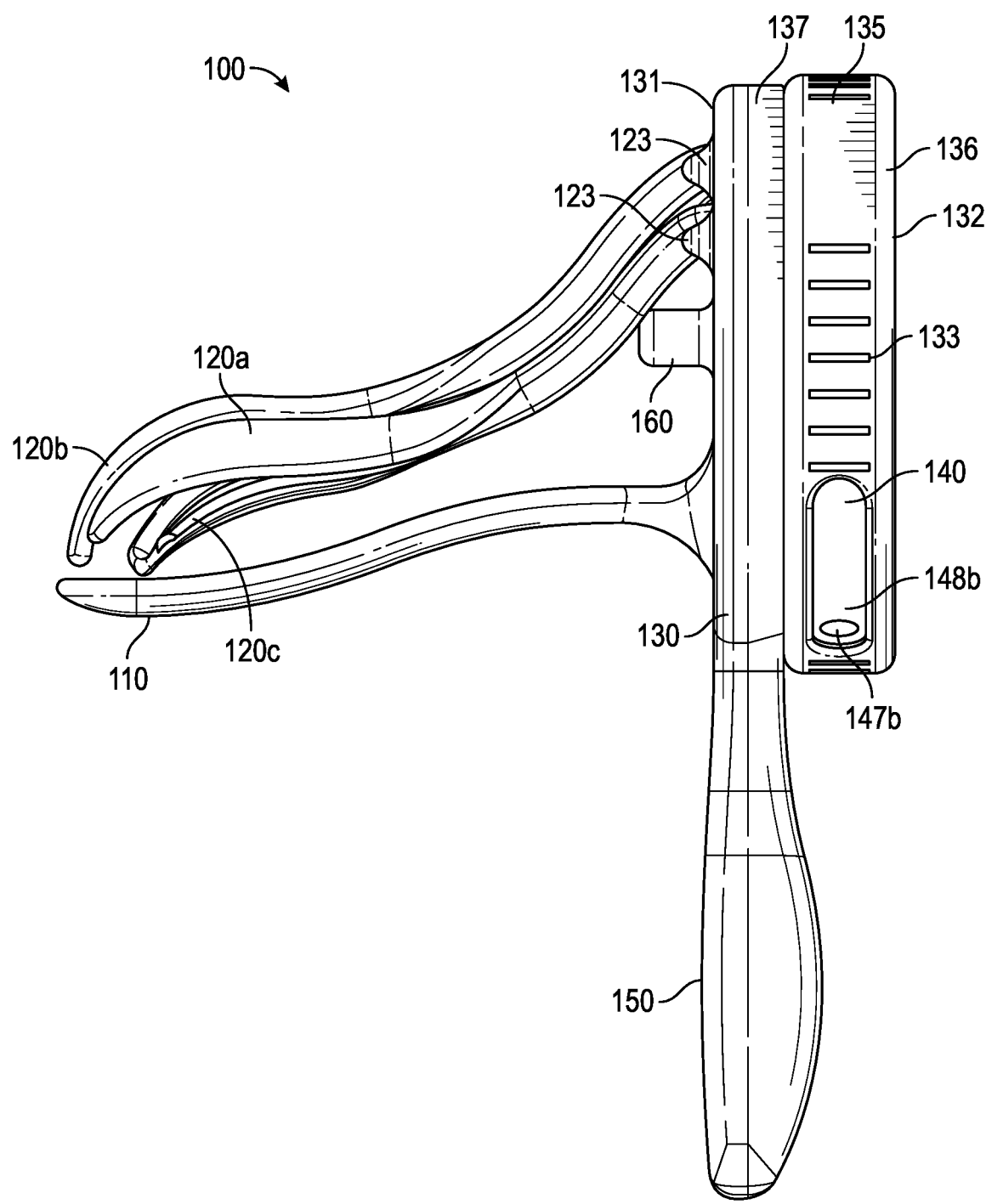
FIG. 7 shows a right plan view of the vaginal speculum in accordance with the first illustrated embodiment.

FIG. 7 shows a right plan view of the vaginal speculum (100) in accordance with the first illustrated embodiment. The vaginal speculum includes a housing (130) having a body (137), a cam housing (135), a cover (136), and an elongated handle (150) coupled therewith. The housing has a proximal surface (132) and a distal surface (131). Coupled to the distal surface is a fixed blade (110) and a plurality of pivoting blades (120a; 120b; 120c) disposed above the fixed blade. Each of the plurality of pivoting blades is coupled to a respective hinge element (123), thereby allowing the plurality of pivoting blades to hingedly move from a collapsed state to an expended state, and back to the collapsed state. A light-guiding element (160) is shown coupled to the distal surface between the plurality of pivoting blades and the fixed blade. Other locations for the light-guiding element may also be utilized to provide sufficient lighting for a physician to have proper viewing.

Contained within the cam housing (135) is a cam plate (140) which is shown partially exposed from a slot (148b). A threaded receiver (147a) is disposed on the cam plate and accessible from the slot. The threaded receiver is configured to receive a lever (not shown), wherein upon coupling of said level allows a user to press the lever and cause the cam plate to rotate. Rotation of the cam plate causes the plurality of pivoting blades to move into either the expanded state or collapsed state depending on direction the lever is actuated.

Figure 8:
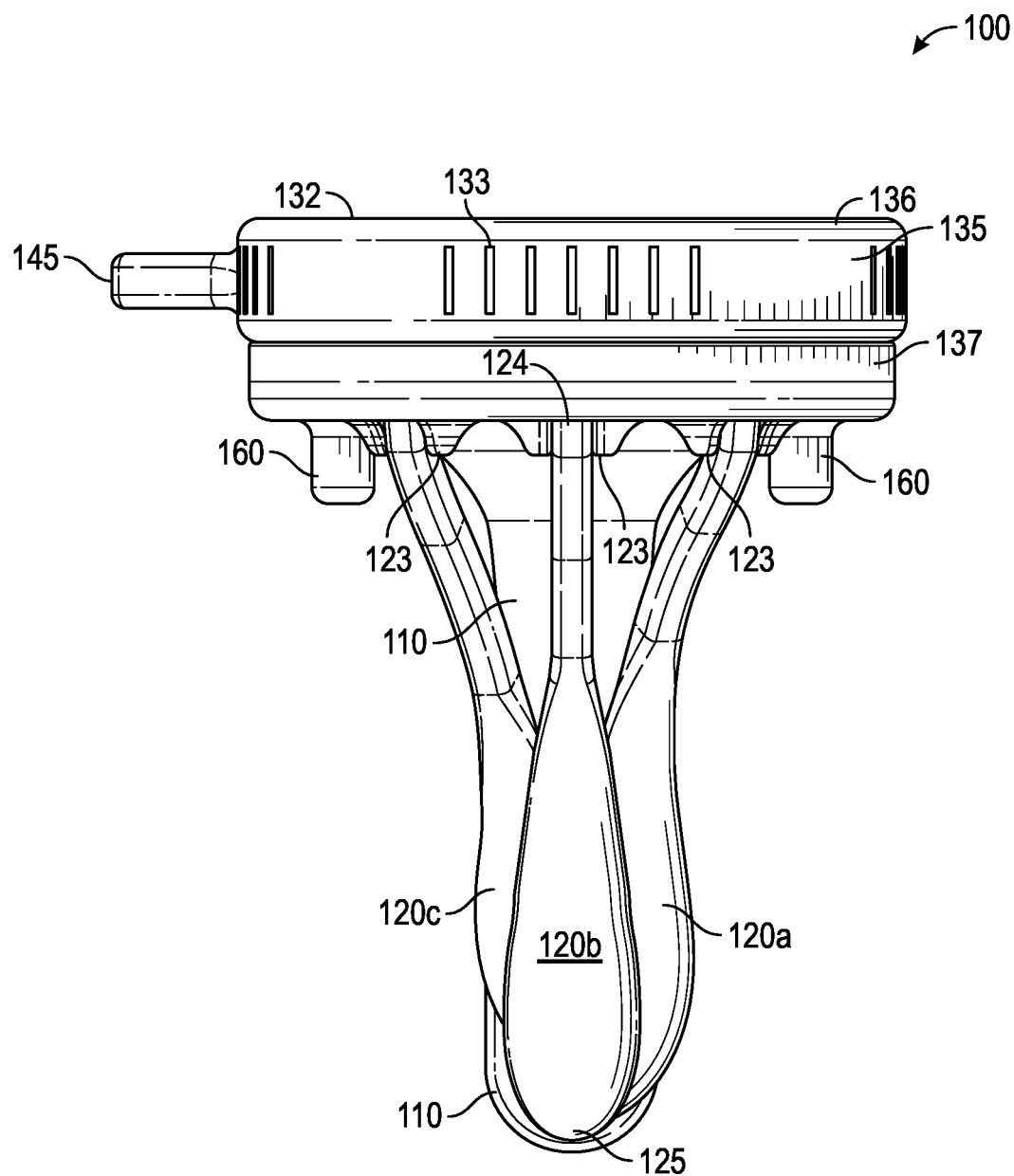
FIG. 8 shows a top plan view of the vaginal speculum in accordance with the first illustrated embodiment.

FIG. 8 shows a top plan view of the vaginal speculum (100) in accordance with the first illustrated embodiment. A plurality of pivoting blades (120a; 120b; 120c), each having a first end (124) and a second end (125), are shown in a collapsed state wherein each of the second end are nested within each other near a fixed blade (110). While in any state, whether collapsed or expanded, each of the first ends are separated from one another and are each coupled to a hinge element (123) which is coupled to a body (137). The body is additionally coupled to a cam housing (135) having a plurality of notches (133). A lever (145) is shown coupled to the cam housing and configured to maneuver the plurality of pivoting blades into an expanded state or a collapsed state. Additionally, a cover (136) is coupled to the cam housing to encapsulate componentry contained therein. A light-guiding element (160) is shown disposed on either side of the plurality of pivoting blades and are likewise coupled to the body.

Figure 9:
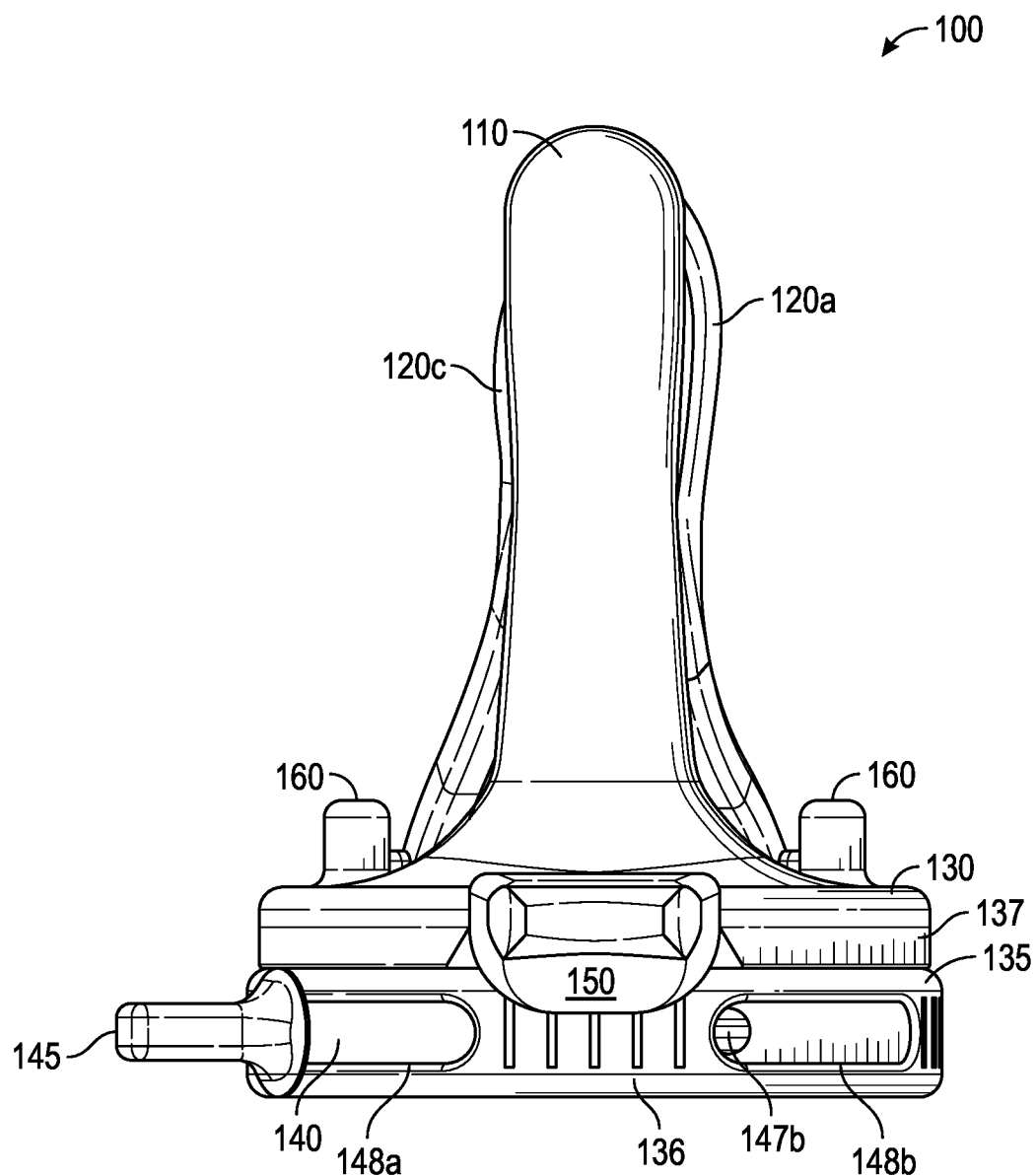
FIG. 9 shows a bottom plan view of the vaginal speculum in accordance with the first illustrated embodiment.

FIG. 9 shows a bottom plan view of the vaginal speculum (100) in accordance with the first illustrated embodiment. The vaginal speculum comprises a fixed blade (110) and a plurality of pivoting blades (120a; 120c) each coupled to a housing (130). The vaginal speculum, as shown, further comprises a lever (145) coupled to the housing and additionally coupled to a cam plate (140) contained with the housing. The lever comprises a threaded member and is configured to couple to a threaded receiver (147a; 147b). The lever is further configured to translate about a slot (148a). In alternate configurations, the lever is coupled to threaded receiver 147b and configured to translate about slot 148b. The lever may be adapted to provide left-hand or right-hand operation, and can be so configured, for example, by installing the threaded member of the lever into the corresponding threaded receiver of the vaginal speculum to render the device as left- or right-hand operable. In some embodiments, the speculum is provided with two threaded receivers. A first threaded receiver is configured for right-hand operation and a second configured for left-hand operation, wherein, with the lever installed in a corresponding receiver the vaginal speculum can be configured for left- or right-handed operation.

Second Illustrated Embodiment—System Including Vaginal Speculum & Insert

Figure 10:
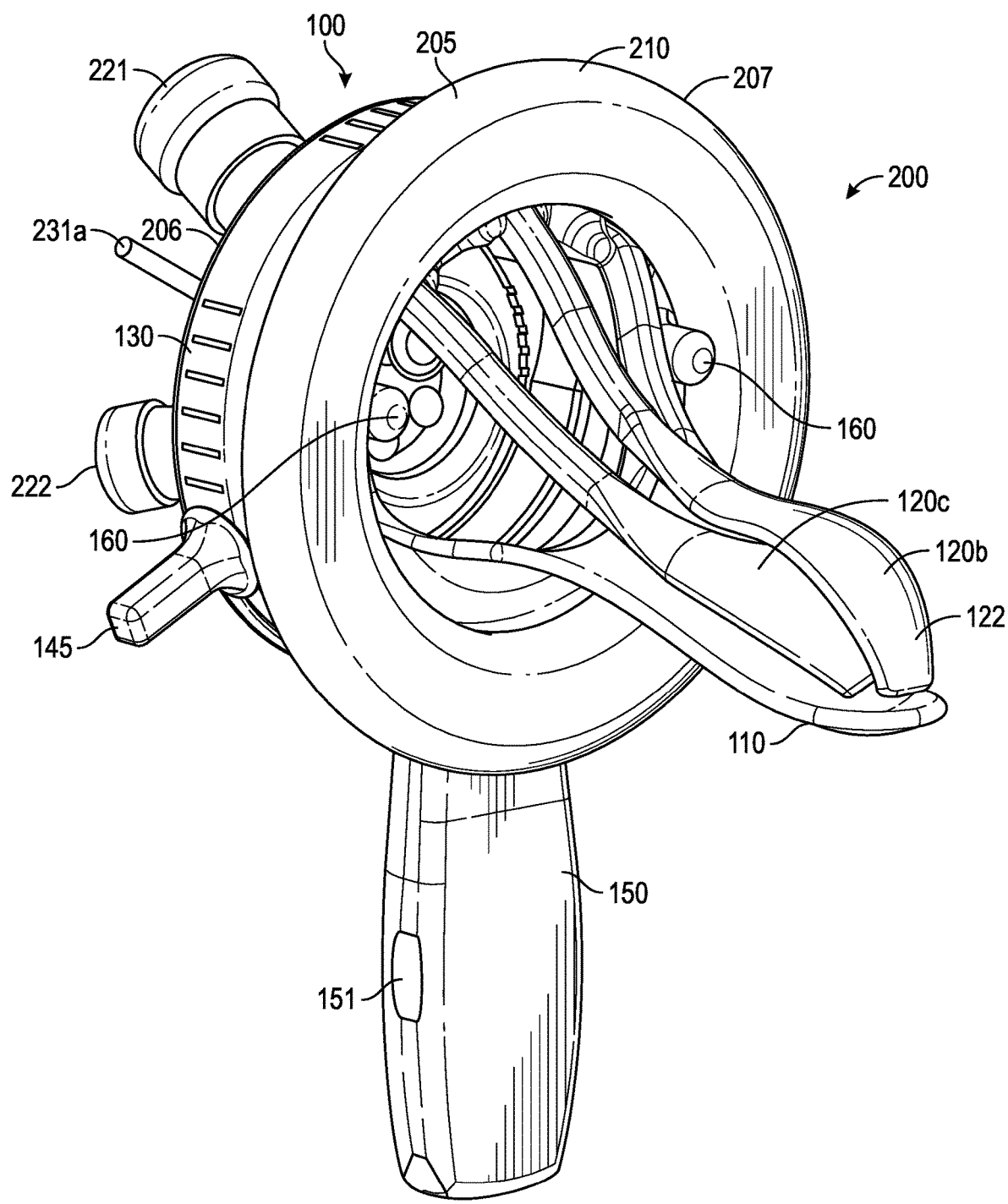
FIG. 10 shows a perspective view of the system, including a front, top, and left-side of the vaginal speculum and insert engaged therewith in accordance with a second illustrated embodiment.
Figure 11:
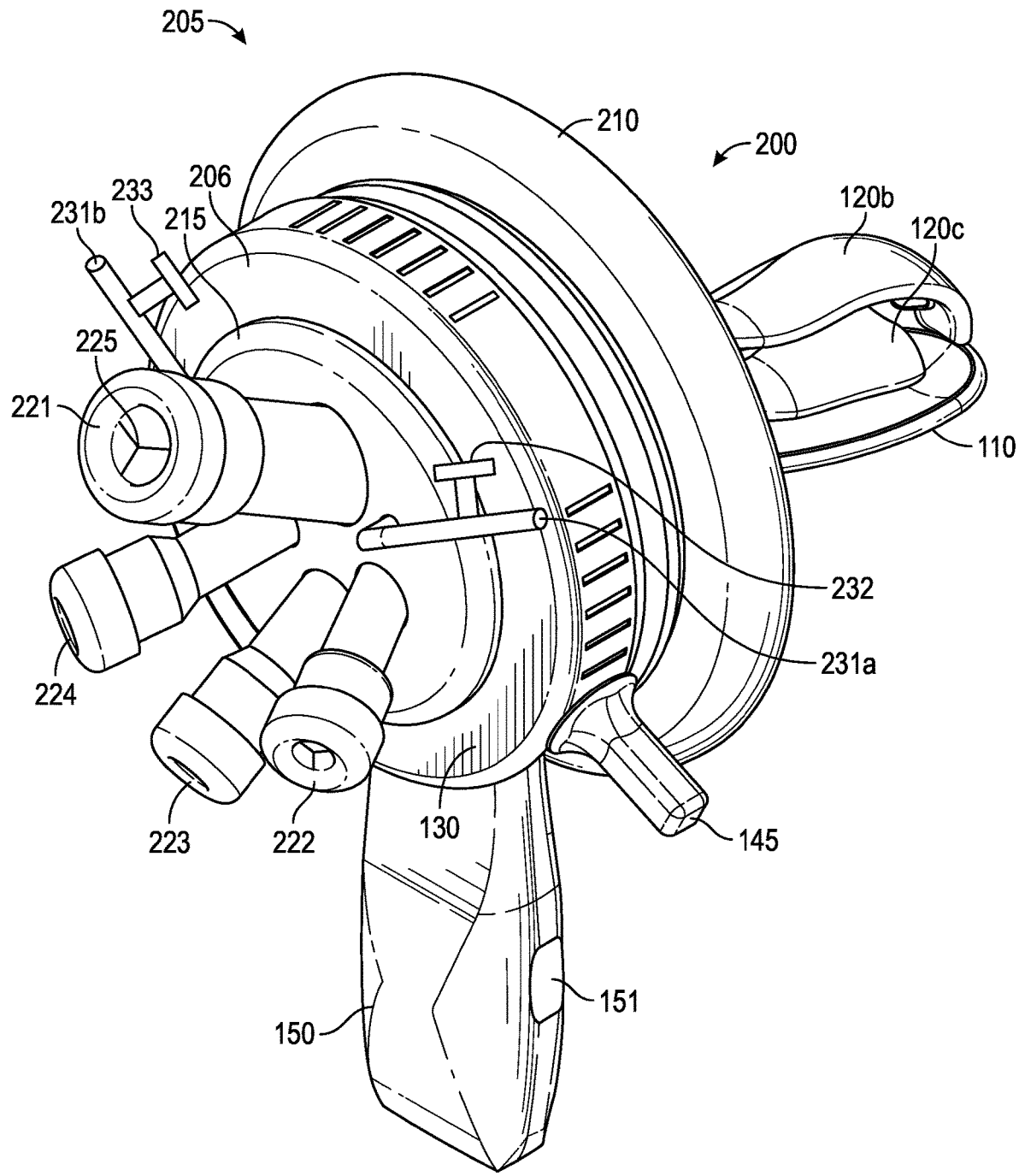
FIG. 11 shows another perspective view of the system, including a rear, top, and right-side of the vaginal speculum and insert engaged therewith in accordance with the second illustrated embodiment.
Figure 12:
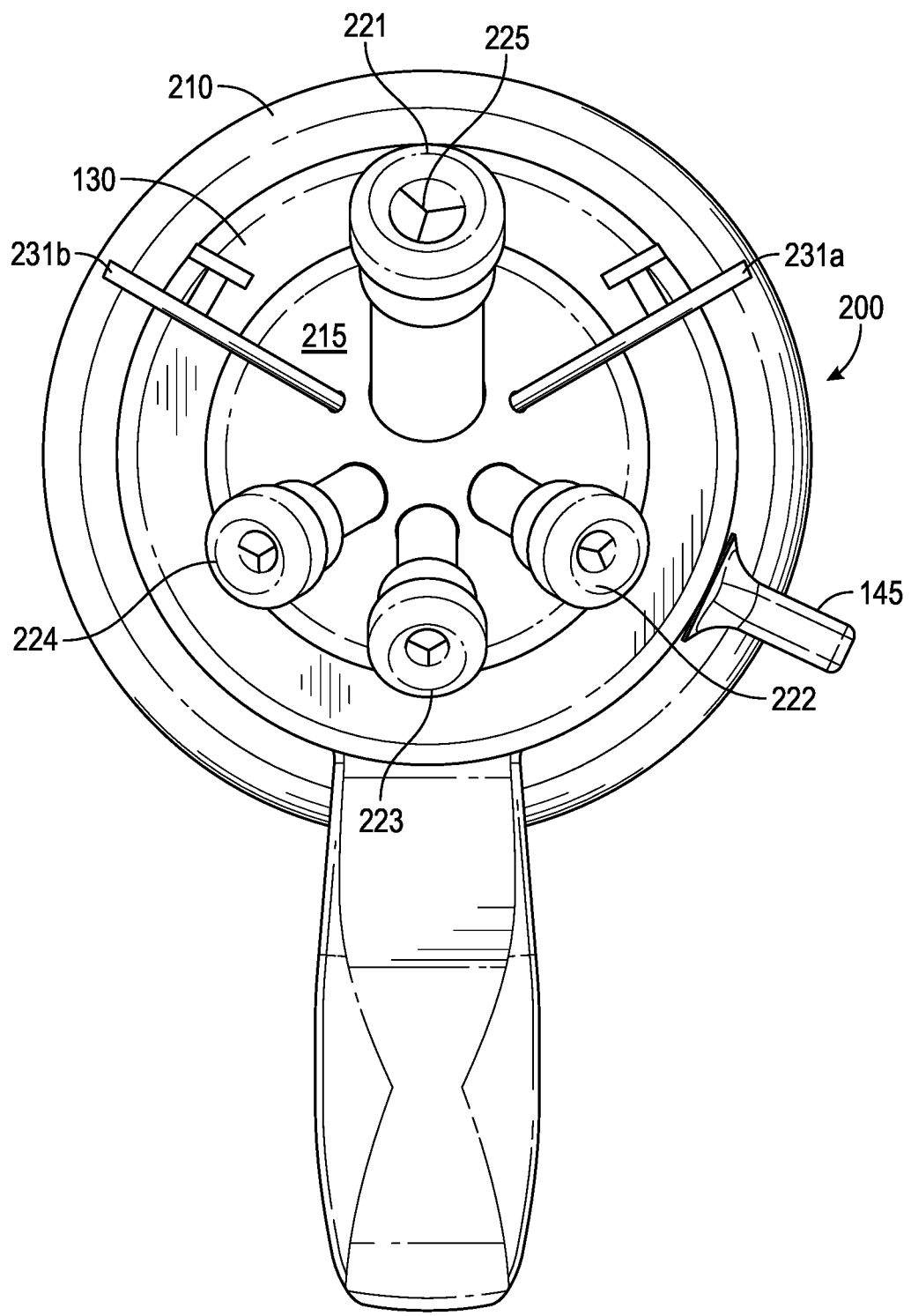
FIG. 12 shows a rear plan view of the system in accordance with the second illustrated embodiment.

Now, utilizing the vaginal speculum as shown in FIGS. 1-9 and described above, a system is formed by engaging an insert with the housing of the vaginal speculum as shown in FIGS. 10-12.

Referring to FIG. 10, a perspective view of the system (200) is provided. An insert (205) is engaged with a vaginal speculum (100) and comprises a vaginal seal (210) disposed at a distal end (207) of the insert, between a housing (130) and spoon elements (122) of the vaginal speculum. The vaginal seal may be configured as a balloon or similar expandable element, such as an inflatable element being inflatable by gas or fluid. The vaginal speculum is inserted, and the spoon elements are expanded, prior to inflating the vaginal seal to form a hermetic seal about the vaginal opening. In this regard, upon deployment of the vaginal seal, the system is secured and configured for performing a medical procedure. The vaginal seal may comprise an annular shape, and may be configured to surround a distal surface of the housing of the vaginal speculum in order to function as a seal at the vaginal opening. The vaginal seal is configured to not obstruct light from a light-guiding element (160), as shown. At a proximal end (206) of the insert each of a plurality of ports (221; 222) and gas/vacuum deployment-elements (231a; 231b, respectively) are disposed.

FIGS. 11-12 show additional views of the system (200), wherein the insert, as shown engaged with a vaginal speculum (100) to form the system, comprises a vaginal seal (210), and a flange (215), wherein a portion of a housing (130) of the vaginal speculum is disposed between the flange and the vaginal seal. Extending from the flange are a plurality of ports (221; 222; 223; and 224), which may be referred to as first through fourth ports, respectively, a gas deployment-elements (231a), and a vacuum deployment-element (231b). In the illustrated example, gas deployment-element 231a comprises a gas valve 232 for deploying gas from an external source into the vaginal cavity during a procedure, the valve is configured to regulate deployment of gas for insufflation. The vacuum deployment-element 231b is provided to remove smoke or other gaseous matter from the vaginal cavity during operation; the vacuum deployment-element further comprises a vacuum valve (233) to regulate provision of vacuum to the cavity. Each of the ports is configured to receive one of a plurality of possible medical instruments, including, for example and without limitation, a hysteroscope, vacuum syringe, endoscope, modified scissors, graspers, stapling device, bipolar cautery device, retractors, suction device, hulka clip applicator, cautery loops for a LEEP procedure. Some of these instruments may need to be modified for use in the vagina. Additionally, each of the ports is shown to comprise a sealing valve 225 for sealing a terminal end of the port when an instrument is not inserted therethrough.

Third Illustrated Embodiment—Alternative System

FIG. 13 shows an alternative system (200), wherein a vaginal speculum (100) is combined with a port attachment (302). Here, the vaginal speculum is provided in accordance with the embodiments described in FIGS. 1-9, and the single port attachment is at least temporarily attached to the vaginal speculum. Note the vaginal speculum is shown to be configured in an expanded state. The single-port attachment generally comprises a clamping arm (301) and a port element (302). The clamping arm and port element may be provided in a myriad of different configurations, assemblies, and implementations; however, the general spirit of the single-port attachment is to provide a single port for receiving and guiding a surgical instrument therethrough. One with the ordinary level of skill in the art will appreciate a number of variations, such as a clamp attachment, magnetic attachment, screw attachment, or otherwise. Moreover, a two-port, three-port or other attachment is within the variations that would be readily appreciated by one having skill in the art upon a review of the instant disclosure.

The system, including a speculum and insert as described in any of the embodiments above, may be used to perform medical procedures, such as, without limitation: Adhesiolysis, Cervical (Cone) Biopsy, Colporrhaphy, Colposcopy, Dilation and Curettage (D&C), Endometrial Ablation, Endometrial or Uterine Biopsy, Fluid-Contrast Ultrasound (FCUS), Hysterectomy, Hysterosalpingography, Hysteroscopy, Myomectomy, Oophorectomy, Pelviscopy (Pelvic Laparoscopy), Selective Salpingography, uterine or vaginal vault suspensions, Toluidine Blue Dye Test, Trachelectomy, Tubal Ligation, Uterine (artery) Fibroid Embolization (UFE), While various details, features, and combinations are described in the instant disclosure, one having skill in the art will appreciate a myriad of possible alternative combinations and arrangements of the features disclosed herein. As such, the descriptions are intended to be enabling only, and non-limiting. Instead, the spirit and scope of the invention is set forth in the appended claims.

FEATURE LIST vaginal speculum (100)
fixed blade (110)
plurality of pivoting blades (120a; 120b; 120c)
follower element (121)
spoon element (122)
hinge element (123)
first end (124)
second end (125)
housing (130)
distal surface (131)
proximal surface (132)
plurality of notches (133)
aperture (134)
cam housing (135)
cover (136)
body (137)
cam plate (140)
groove (141)
lever (145)
threaded member (146)
threaded receiver (147a; 147b)
slot (148a; 148b)
elongated handle (150)
actuator (151)
light-guiding element (160)
system (200)
insert (205)
proximal end (206)
distal end (207)
vaginal seal (210)
flange (215)
plurality of ports (221; 222; 223; 224)
sealing valve (225)
gas deployment-element (231a)
vacuum deployment-element (231b)
gas valve (232)
vacuum valve (233)
port attachment (300)
clamping arm (301)
port element (302)

What is claimed is:

1. A system for performing a medical procedure comprising:
   a vaginal speculum comprising:
      a housing having a distal surface and a proximal surface,
      an aperture extending through the housing from the distal surface to the proximal surface,
      a fixed blade coupled to the distal surface,
      a plurality of pivoting blades each hingedly coupled to the distal surface,
         the plurality of pivoting blades each comprises a follower element at a first end and a spoon element at a second end, and
      a cam plate disposed within the housing,
         the cam plate comprises a plurality of grooves, wherein each follower element is configured to engage with one of the plurality of grooves,
      wherein the plurality of pivoting blades is configured to expand or collapse relative to the fixed blade upon rotation of the cam plate; and
   an insert having a proximal end and a distal end,
      the insert comprises a plurality of ports at the proximal end, and a vaginal seal at the distal end disposed on the distal surface of the housing wherein the vaginal seal is configured to form a hermetic seal about a vaginal opening.

2. The system of claim 1, wherein the vaginal seal comprises an annular shape that surrounds the fixed blade and each of the plurality of pivoting blades.

3. The system of claim 2, the vaginal seal further comprising an opening wherein the fixed blade and each of the plurality of pivoting blades extend through the opening.

4. The system of claim 1, the insert further comprising a gas deployment-element disposed at the proximal end, wherein the gas deployment-element is configured to deploy gas from an external source into a vaginal cavity during a procedure.

5. The system of claim 1, the insert further comprising a vacuum deployment-element disposed at the proximal end, wherein the vacuum deployment-element is configured to remove gaseous matter from a vaginal cavity.

6. The system of claim 1, wherein the spoon element of each of the plurality of pivoting blades comprises a greater width than the respective first end.

7. The system of claim 1, wherein the vaginal seal is inflatable.

* * * * *